(12) United States Patent
Genin et al.

(10) Patent No.: US 11,180,503 B2
(45) Date of Patent: Nov. 23, 2021

(54) [1,2,4]TRIAZOLO[4,3-A]PYRAZIN-6(5H)-ONE DERIVATIVES

(71) Applicant: Eli Lilly and Company, Indianapolis, IN (US)

(72) Inventors: Michael James Genin, Danville, IN (US); William Glen Holloway, Brownsburg, IN (US); Richard Duane Johnston, Greenfield, IN (US); John Richard Morphy, Surrey (GB); Qing Shi, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 42 days.

(21) Appl. No.: 16/624,545

(22) PCT Filed: Jul. 26, 2018

(86) PCT No.: PCT/US2018/043845
§ 371 (c)(1),
(2) Date: Dec. 19, 2019

(87) PCT Pub. No.: WO2019/027783
PCT Pub. Date: Feb. 7, 2019

(65) Prior Publication Data
US 2020/0123154 A1   Apr. 23, 2020

Related U.S. Application Data

(60) Provisional application No. 62/540,122, filed on Aug. 2, 2017.

(51) Int. Cl.
*C07D 471/14* (2006.01)
*A61K 31/4985* (2006.01)

(52) U.S. Cl.
CPC ................. *C07D 471/14* (2013.01)

(58) Field of Classification Search
CPC .... C07D 471/14; A61K 31/4985; A61P 13/12
USPC .......................................... 544/346; 514/250
See application file for complete search history.

(56) References Cited

U.S. PATENT DOCUMENTS

| | | |
|---|---|---|
| 8,299,080 B2 | 10/2012 | Okada et al. |
| 9,175,010 B2 | 11/2015 | Branstetter et al. |
| 9,868,741 B2 | 1/2018 | Jesudason |
| 10,138,244 B2 | 11/2018 | Rekhter et al. |
| 2010/0048556 A1 | 2/2010 | Okada et al. |

FOREIGN PATENT DOCUMENTS

| | | |
|---|---|---|
| EP | 0040401 A1 | 11/1981 |
| EP | 2103613 A1 | 9/2009 |
| EP | 2615096 A1 | 7/2013 |
| WO | 2008/103357 A1 | 8/2008 |
| WO | 2016/55618 A1 | 4/2016 |
| WO | 2017/139186 A1 | 8/2017 |
| WO | 2018/039051 A1 | 3/2018 |

OTHER PUBLICATIONS

Al-Salahi, Rashad, "Synthesis of Novel 2-Alkoxy(aralkoxy)-4H-[1,2,4]triazolo[1,5-a]quinazolin-5-ones Starting with Dialkyl-N-Cyanoimidocarbonates," Journal of Heterocyclic Chemistry, 2011, vol. 48, pp. 656.

Unciti-Broceta, Asier, "Regioselective One-Pot synthesis of 9-Alkyl-6-chloropyrido[3,2-e][1,2,4]Triazolo-[4,3-a]Pyrazines," the Journal of Organic chemistry, vol. 70(7), pp. 2878-2880, 2005.

*Primary Examiner* — Charanjit Aulakh
(74) *Attorney, Agent, or Firm* — Quarles & Brady LLP

(57) ABSTRACT

The present invention provides a compound of Formula (I), wherein X is H or C1-C3 alkyl optionally substituted with hydroxyl; Y is H, hydroxy, or methyl; R is ethyl, n-propyl, cyclopropyl, or Formula (II); and A is methyl, cyclopropyl or trifluoromethyl; or a pharmaceutically acceptable salt thereof; with the proviso that when X and Y are both H and R is n-propyl, then A is other than methyl; for use as a human PDE1 inhibitor.

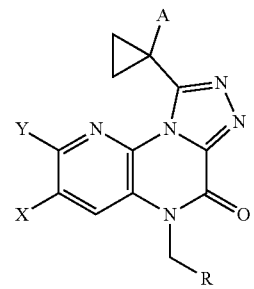

(I)

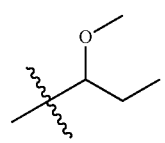

(II)

12 Claims, No Drawings

[1,2,4]TRIAZOLO[4,3-A]PYRAZIN-6(5H)-ONE DERIVATIVES

The present invention relates to certain human PDE1 inhibitors, to pharmaceutical compositions comprising the compounds, to methods of using the compounds to treat physiological disorders, and to intermediates and processes useful in the synthesis of the compounds.

Phosphodiesterases (PDEs) are enzymes that regulate the cellular levels of cAMP and cGMP by controlling the rate at which these cyclic nucleotides are hydrolyzed. PDE1, a calcium and calmodulin-dependent PDE, is one of at least 11 known PDE families. PDE1 is expressed in many tissues, including the brain, heart, lung, kidney, and smooth muscle. In addition, PDE1 is comprised of a family of three known isoforms, PDE1A, PDE1B, and PDE1C.

Patients suffering from diabetes often develop a form of chronic kidney disease referred to as diabetic kidney disease (or diabetic nephropathy). It has been estimated that diabetic kidney disease may affect as many as 40 percent of diabetic patients. Treatment options for diabetic kidney disease is limited and includes use of medications that lower blood pressure, management of blood glucose levels, diet, and weight, and implementation of regular physical activity. Thus, there is a need for additional treatment choices for patients suffering from chronic kidney disease, particularly diabetic kidney disease.

U.S. Pat. No. 8,299,080 discloses certain quinoxaline derivatives having PDE9 inhibiting activity useful for treating various disorders such as dysuria and hypertension. In addition, European Patent No. 0 040 401 discloses certain substituted triazoloquinoxalin-4-ones possessing anti-hypertensive activity.

The present invention provides certain novel compounds that are inhibitors of human PDE1. In addition, the present invention provides certain novel compounds that are selective inhibitors of human PDE1A, PDE1B, and PDE1C relative to other human PDEs, such as PDE3A, PDE4D, and PDE6AB. Furthermore, the present invention provides certain novel compounds that may have antihypertensive effects and may also improve renal blood flow. In addition, certain compounds of the present invention may reduce renal fibrosis.

Accordingly, the present invention provides a compound of Formula I:

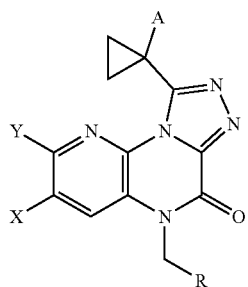

Formula I wherein X is H or C1-C3 alkyl optionally substituted with hydroxyl;

Y is H, hydroxy, or methyl;
R is ethyl, n-propyl, cyclopropyl, or

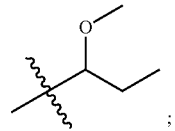 [SMILES: *C(CC)OC]

and
A is methyl, cyclopropyl or trifluoromethyl;
or a pharmaceutically acceptable salt thereof;
with the proviso that when X and Y are both H and R is n-propyl, then A is other than methyl.

The present invention also provides a method of treating chronic kidney disease in a patient, comprising administering to a patient in need of such treatment an effective amount of a compound of Formula I.

The present invention also provides a method of treating diabetic kidney disease in a patient, comprising administering to a patient in need of such treatment an effective amount of a compound of Formula I.

The present invention also provides a method of treating hypertension in a patient, comprising administering to a patient in need of such treatment an effective amount of a compound of Formula I.

In addition, the invention provides a compound of Formula I for use in therapy. The invention further provides a compound of Formula I for use in for the treatment of chronic kidney disease. In addition, the invention provides a compound of Formula I for use in the treatment of diabetic kidney disease. In addition, the invention provides a compound of Formula I for use in the treatment of hypertension. Furthermore, the invention provides the use of a compound of Formula I for the manufacture of a medicament for the treatment of chronic kidney disease. Furthermore, the invention provides the use of a compound of Formula I for the manufacture of a medicament for the treatment of diabetic kidney disease. The invention further provides the use of a compound of Formula I for the manufacture of a medicament for the treatment of hypertension.

The invention further provides a pharmaceutical composition, comprising a compound of Formula I with one or more pharmaceutically acceptable carriers, diluents, or excipients. The invention further provides a process for preparing a pharmaceutical composition, comprising admixing a compound of Formula I with one or more pharmaceutically acceptable carriers, diluents, or excipients. This invention also encompasses novel intermediates and processes for the synthesis of compounds of Formula I.

As used herein, the terms "treating", "treatment", or "to treat" includes prohibiting, restraining, slowing, stopping, or reversing the progression or severity of an existing symptom or disorder.

As used herein, the term "patient" refers to a mammal, such as a dog or a human, with a human being preferred.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

As used herein the term "C1-C3 alkyl" refers to methyl, ethyl, n-propyl, and isopropyl.

An effective amount can be readily determined by one skilled in the art using known techniques and by observing results obtained under analogous circumstances. In determining the effective amount for a patient, a number of factors are considered by one skilled in the art, including, but not limited to: the patient's size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

Compounds of the present invention are effective at a dosage per day that falls within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are formulated as pharmaceutical compositions administered by any route which makes the compound bioavailable, including oral and parenteral routes. Most preferably, such compositions are for oral administration. Such pharmaceutical compositions and processes for preparing same are well known in the art (See, e.g., Remington: The Science and Practice of Pharmacy, L. V. Allen, Editor, 22$^{nd}$ Edition, Pharmaceutical Press, 2012).

The compounds of Formula I are particularly useful in the treatment methods of the invention, but certain groups, substituents, and compounds are preferred. The following paragraphs describe such preferred groups, substituents, and compounds. It will be understood that these preferences are applicable both to the treatment methods and to the new compounds of the invention.

It is preferred that Y is H.
It is preferred that X is methyl.
It is preferred that R is n-propyl.
It is preferred that A is cyclopropyl.
It is preferred that the compounds of Formula I are in the free base form.
It is further preferred that when Y is H, X is methyl.
It is further preferred that when Y is H, R is n-propyl.
It is further preferred that when Y is H, A is cyclopropyl.
It is further preferred that when X is methyl, R is n-propyl.
It is further preferred that when X is methyl, A is cyclopropyl.
It is especially preferred that when Y is H, X is methyl and A is cyclopropyl.
It is especially preferred that when Y is H, X is methyl and R is n-propyl.
It is especially preferred that Y is H, R is n-propyl and A is cyclopropyl.
The compound of the formula:

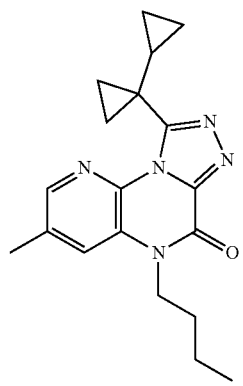

and the pharmaceutically acceptable salts thereof are most preferred with the free base of the compound directly above being most especially preferred.

A pharmaceutically acceptable salt of the compound of the invention may be formed, for example, by reaction of an appropriate free base of the compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography under specified conditions, first and second, respectively.

Certain abbreviations are defined as follows: "ACN" refers to acetonitrile; "AcOH" refers to glacial acetic acid; "DBU" refers to 1,8-diazabicyclo[5.4.0]undec-7-ene; "DCM" refers to dichloromethane or methylene chloride; "DIPEA" refers to N,N-diisopropylethylamine; "DMF" refers to N,N-dimethylformamide; "DMSO" refers to dimethylsulfoxide; "EDCI" refers to 1-ethyl-3-(3-dimethylaminopropyl)carbodiimide; "ES/MS" refers to Electrospray Mass Spectrometry; "EtOAc" refers to ethyl acetate; "Et$_2$O" refers to diethyl ether; "EtOH" refers to ethanol; "HMDS" refers to hezamethyldisilazane; "HOBT" refers to hydroxybenzotriazole; "IPA" refers to isopropanol; "HATU" refers to 1-[bis(dimethylamino)methylene]-1H-1,2,3-triazolo[4,5-b]pyridinium 3-oxid hexafluorophosphate; "RBF" refers to round bottomed flask; "TR" refers to retention time; "hr" refers to hour or hours; "IC$_{50}$" refers to the concentration of an agent that produces 50% of the maximal inhibitory response possible for that agent; "µmol" refers to micromole or micromoles; "min" refers to minute or minutes; "MeOH" refers to methanol or methyl alcohol; "MTBE" refers to methyl-tert-butyl ether; "NiNTA" refers to chromatography with an agarose stationary phase functionalized with nitrilotriacetic acid as chelator; "POCl$_3$" refers to phosphorus oxychloride; "RT" refers to room temperature; "SNAr" refers to nucleophilic aromatic substitution; "TEA" refers to triethylamine; "THF" refers to tetrahydrofuran; "Tris" refers to 2-Amino-2-hydroxymethyl-propane-1,3-diol; "U/ml" refers to units per milliliter; "wt" refers to weight; and "Pd-PEPPSI-IHeptCl" refers to dichloro[1,3-bis(2,6-di-4-heptylphenyl)imidazol-2-ylidene](3-chloropyridyl)palladium(II).

The compounds of the present invention may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention. The products of each step below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

PREPARATION 1

Synthesis of
3-N-butyl-5-methyl-pyridine-2,3-diamine

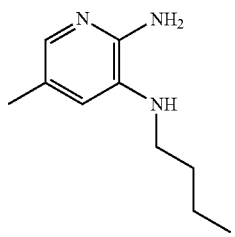

To a stirred suspension of 5-methylpyridine-2,3-diamine (5.64 g, 44.0 mmol) in DCM (300 mL) is added butanal (3.28 g, 46 mmol) and AcOH (0.26 mL, 4.5 mmol). The suspension is stirred for 50 min at RT then sonicated for 1 min. Sodium triacetoxyborohydride (29.1 g, 137 mmol) is added in 5 portions and the reaction mixture is stirred at room temperature for 45 min. The reaction mixture is quenched with water (300 mL) and the layers are separated. The aqueous is diluted with satd. aq. NaHCO$_3$ solution and extracted with DCM. The combined organics are washed with satd. aq. NaHCO$_3$ solution, sat. aq. NaCl solution, then dried over anhydrous Na$_2$SO$_4$ and further dried over anhydrous MgSO$_4$, filtered, and concentrated under reduced pressure to give the title compound 5.64 g as a crude material. The aq. NaHCO$_3$ and sat. aq. NaCl washes are combined, diluted with sat. aq. NaCl solution and extracted with 3:1 CHCl$_3$/IPA (4×) and with MTBE. The organics are combined, washed with sat. aq. NaCl solution, dried over anhydrous MgSO$_4$, filtered, and concentrated under reduced pressure to afford additional 780 mg of material. Materials are combined to give crude title compound (6.42 g). MS (m/z): 180 (M+H).

Prepare the following compounds as shown in Table 1 in a manner essentially analogous to the method of Preparation 1 from 5-methylpyridine-2,3-diamine and propanal (for Prep. No. 2); and 5-bromo-6-methyl-pyridine-2,3-diamine and butanal (for Prep. No. 3).

TABLE 1

| Prep. No. | Chemical Name | Structure | MS (m/z) |
|---|---|---|---|
| 2 | 5-Methyl-3-N-propyl-pyridine-2,3-diamine | 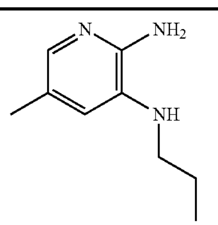 | 166 (M + H) |

TABLE 1-continued

| Prep. No. | Chemical Name | Structure | MS (m/z) |
|---|---|---|---|
| 3 | 5-Bromo-3-N-butyl-6-methyl-pyridine-2,3-diamine | 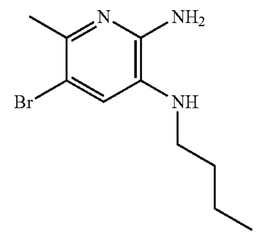 | 258/260 (M + H) |

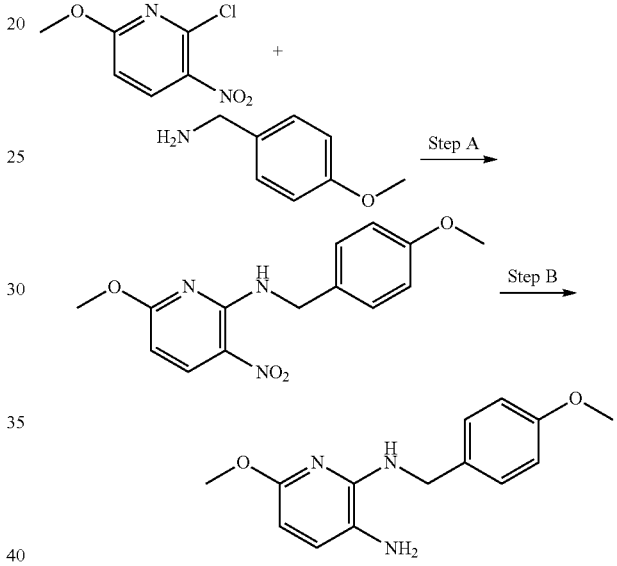

Scheme 1

PREPARATION 4

Synthesis of 6-methoxy-N-[(4-methoxyphenyl)methyl]-3-nitro-pyridin-2-amine

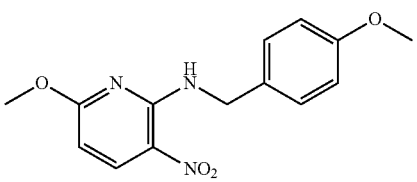

Scheme 1, Step A: A solution of 2-chloro-6-methoxy-3-nitro-pyridine (4.99 g, 26.515 mmol) in ACN (90 mL) is stirred under nitrogen and is heated to 65° C. 4-Methoxybenzylamine (7.25 mL, 55.5 mmol) is added and a solid precipitate forms. The reaction is stirred at 65° C. for 1 hr. The reaction mixture is cooled to RT, filtered through a pad of diatomaceous earth, concentrated under reduced pressure, and then further dried under high vacuum overnight to give a crude yellow solid title compound (8.638 g). MS (m/z): 290 (M+H).

PREPARATION 5

Synthesis of 6-methoxy-2-N-[(4-methoxyphenyl)methyl]pyridine-2,3-diamine

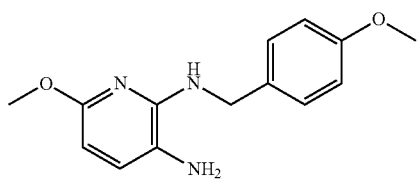

Scheme 1, Step B: 6-Methoxy-N-[(4-methoxyphenyl)methyl]-3-nitro-pyridin-2-amine (5.00 g, 14.0 mmol), bis(pinacolato)diboron (11.2 g, 43.2 mmol) and potassium tert-butoxide (1.93 g, 16.8 mmol) are combined in IPA (55 mL). The reaction mixture is sealed under nitrogen gas and stirred at 110° C. overnight. The reaction is cooled to RT and diluted with EtOAc. The organic layer is washed with water followed by sat. aq. NaCl solution, dried over anhydrous MgSO₄, filtered, and concentrated under reduced pressure. The residue is purified by flash chromatography on silica, eluting with 30-50% EtOAc in hexanes. The pure chromatography fractions are combined and concentrated under reduced pressure, drying under high vacuum overnight to give the crude blue residue title compound (4.88 g). MS (m/z): 260 (M+H).

Scheme 2

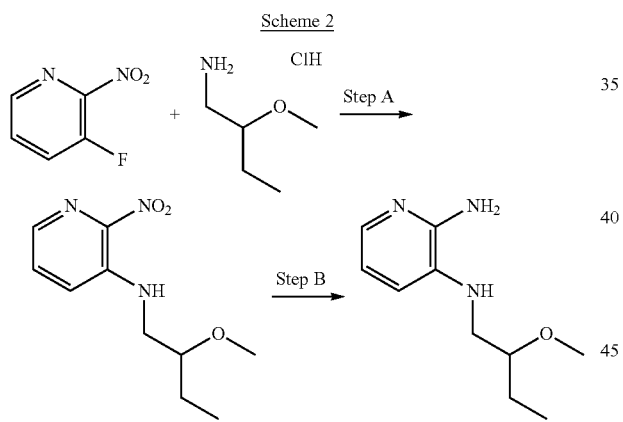

PREPARATION 6

Synthesis of rac-N-(2-methoxybutyl)-2-nitropyridin-3-amine

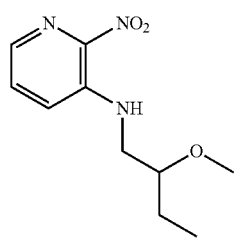 [SMILES: CCC(CNc1cccnc1[N+](=O)[O-])OC]

Scheme 2, Step A: TEA (4.3 mL, 31 mmol) is added to a suspension of 3-fluoro-2-nitropyridine (1.500 g, 10.24 mmol) and (2-methoxybutyl)amine hydrochloride (1.590 g, 10.82 mmol). The reaction is stirred for 2.5 hr at RT. EtOAc is added and the material is washed with sat. aq. NH₄Cl solution and sat. aq. NaCl solution, then dried over anhydrous MgSO₄ and filtered. The filtrate is concentrated and purified by flash chromatography on silica, eluting with DCM/MTBE. The pure chromatography fractions are combined and concentrated under reduced pressure to give a yellow-orange liquid as the title compound (2.223 g; racemate). MS (m/z): 226.0 (M+H).

PREPARATION 7

Synthesis of rac-3-N-[2-methoxybutyl]pyridine-2,3-diamine

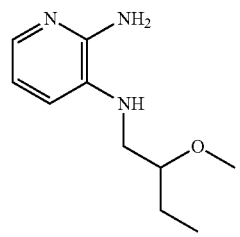

Scheme 2, Step B: MeOH (100 mL) is added to a Parr shaker with 5% Pd/C (0.452 g, 4.25 mmol) under nitrogen, then a solution of N-(2-methoxybutyl)-2-nitro-pyridin-3-amine (2.22 g, 9.86 mmol) in MeOH (100 mL) is added. The Parr shaker is sealed, purged with nitrogen, purged with hydrogen and pressurized (60 psig) with hydrogen, and then stirred at RT for 4 hr. The material is filtered and concentrated to give a dark, thick gel as the title compound (1.794 g; racemate). MS (m/z): 196.0 (M+H).

Scheme 3

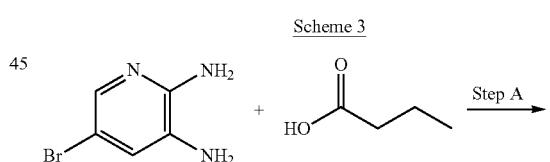

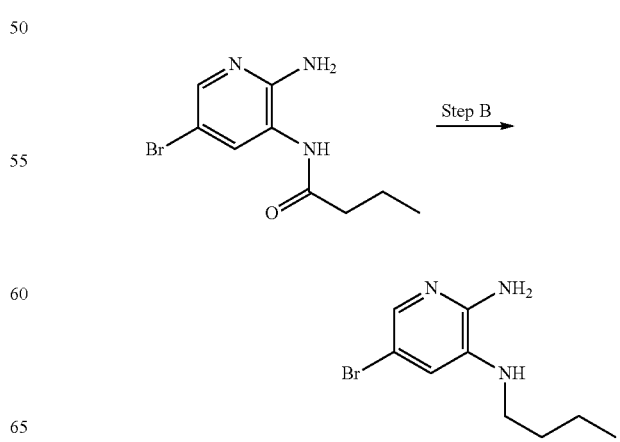

PREPARATION 8

Synthesis of
N-(2-amino-5-bromo-3-pyridyl)butanamide

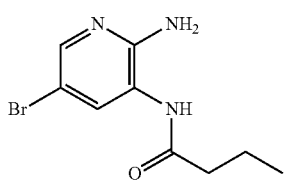

Scheme 3, Step A: 5-Bromopyridine-2,3-diamine (5 g, 27 mmol) followed by DIPEA (14 mL, 80 mmol) are added to a solution of butyric acid (2.7 mL, 29 mmol) and HATU (15.01 g, 40 mmol) in DMF (90 mL). The reaction is sealed under nitrogen and stirred at 50° C. overnight. The reaction mixture is cooled to RT, diluted with water and extracted with EtOAc. The organic phases are combined, washed with satd. aq. NaHCO$_3$, 5% aq. lithium chloride, and sat. aq. NaCl solution then dried over anhydrous MgSO$_4$, filtered, and concentrated under reduced pressure. The residue is purified by flash chromatography on silica, eluting with 40-100% EtOAc in hexanes to give a white-brown solid. The solid is triturated in EtOAc, filtered and dried under vacuum at 50° C. for 1 hr to give the title compound (3.607 g). MS (m/z): 258/260 (M+H).

PREPARATION 9

Synthesis of
5-bromo-3-N-butyl-pyridine-2,3-diamine

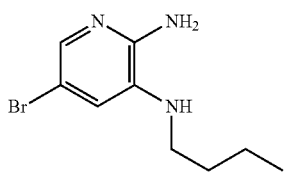

Scheme 3, Step B: A solution of lithium aluminum hydride (30 mL, 1 mol/L in THF) in THF (40 mL) is cooled to −78° C. in an oven-dried three-necked RBF. N-(2-amino-5-bromo-3-pyridyl)butanamide (2.50 g, 9.69 mmol) in THF (40 mL) is added dropwise over 2 hr. The reaction mixture is allowed to warm to room temperature over 3 hr, then stirred at RT overnight. The reaction mixture is cooled to 0° C. in an ice bath. Water (3.0 mL), 2N aq. NaOH (3.75 mL), and water (9.0 mL) are added dropwise sequentially followed by anhydrous MgSO$_4$ and the reaction mixture is stirred for 5 min. The solution is filtered through a pad of diatomaceous earth and rinsed with Et$_2$O. The filtrate is diluted with Et$_2$O and washed with sat. aq. NaCl solution. The organic layer is dried over anhydrous MgSO$_4$, filtered and concentrated under reduced pressure to give the crude title compound (2.28 g). MS (m/z): 244/246 (M+H).

Scheme 4

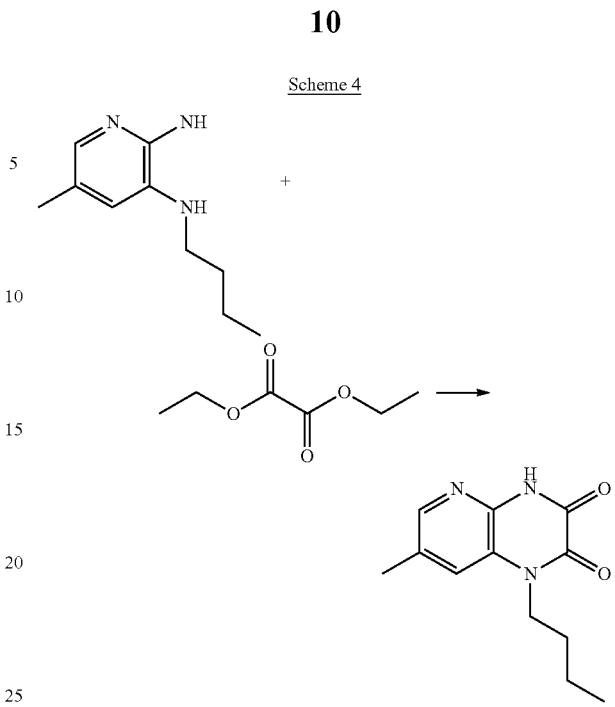

PREPARATION 10

Synthesis of 1-butyl-7-methyl-4H-pyrido[2,3-b]
pyrazine-2,3-dione

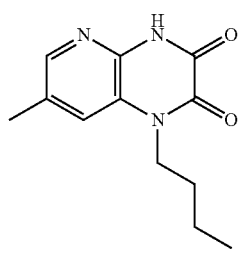 [SMILES: CCCCn1c(=O)c(=O)[nH]c2ncc(C)cc21]

Scheme 4: 3-N-butyl-5-methyl-pyridine-2,3-diamine (5.64 g, 16.0 mmol) in excess diethyl oxalate (30 mL, 220.9 mmol) is split equally between two microwave vials and heated at 120° C. while stirring and vented to the atmosphere under a stream of nitrogen for 1.75 hr. The reaction mixture is cooled to RT. The solids are collected via vacuum filtration and the filter-cake is rinsed with MTBE (2×5 mL). The solid is air-dried for 30 min, then dried at 50° C. under high vacuum to afford a solid (2.198 g). The filtrate is concentrated and purified by flash chromatography on silica, eluting with hexanes/EtOAc. The pure chromatography fractions are combined and concentrated under reduced pressure to give additional solid. The solids combined to give the title compound (2.677 g). MS (m/z): 234 (M+H).

Prepare the following compounds shown in Table 2 from 6-methoxy-2-N-[(4-methoxyphenyl)methyl]pyridine-2,3-diamine (for Prep. No. 11). 5-bromo-3-N-butyl-pyridine-2,3-diamine (for Prep. No. 12); 5-bromo-3-N-butyl-6-methyl-pyridine-2,3-diamine (for Prep. No. 13); 6-methylpyridine-2,3-diamine (for Prep. No. 14); 5-methyl-3-N-propyl-pyridine-2,3-diamine (for Prep. No. 15); rac-3-N-[2-methoxybutyl]pyridine-2,3-diamine (for Prep. No. 16) in a manner essentially analogous to the method of Preparation 10 using a molar excess of diethyl oxalate.

TABLE 2

| Prep. No. | Chemical Name | Structure | MS (m/z) | Notes |
|---|---|---|---|---|
| 11 | 6-Methoxy-4-[(4-methoxyphenyl)methyl]-1H-pyrido[2,3-b]pyrazine-2,3-dione | 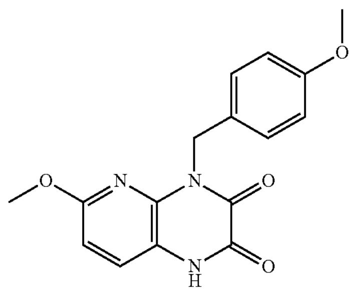 | 314 (M + H) | |
| 12 | 7-Bromo-1-butyl-4H-pyrido[2,3-b]pyrazine-2,3-dione | 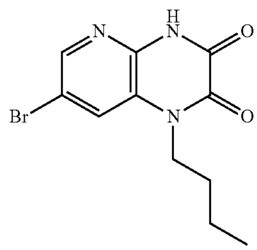 [SMILES: CCCCn1c(=O)c(=O)[nH]c2ncc(Br)cc21] | 298/300 (M + H) | |
| 13 | 7-Bromo-1-butyl-6-methyl-4H-pyrido[2,3-b]pyrazine-2,3-dione | 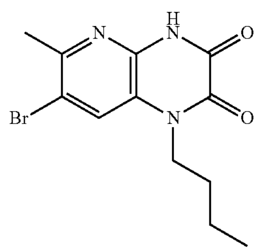 [SMILES: CCCCn1c(=O)c(=O)[nH]c2nc(C)c(Br)cc21] | 312/314 (M + H) | |
| 14 | 6-Methyl-1,4-dihydropyrido[2,3-b]pyrazine-2,3-dione | 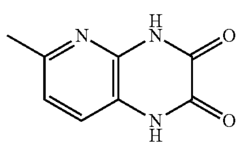 | 178 (M + H) | |
| 15 | 1-Propyl-7-methyl-4H-pyrido[2,3-b]pyrazine-2,3-dione | 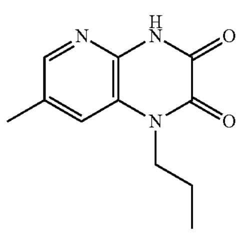 [SMILES: CCCn1c(=O)c(=O)[nH]c2ncc(C)cc21] | 220 (M + H) | Sodium (2 eq.) in EtOH used |
| 16 | rac-1-[2-Methoxybutyl]-4H-pyrido[2,3-b]pyrazine-2,3-dione | 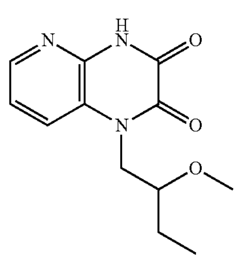 [SMILES: CCC(Cn1c(=O)c(=O)[nH]c2ncccc21)OC] | 250 (M + H) | Sodium methoxide (25%, 2 eq.) in EtOH used |

PREPARATION 17

Synthesis of 1-(cyclopropylmethyl)-6-methoxy-4-[(4-methoxyphenyl)methyl]pyrido[2,3-b]pyrazine-2,3-dione

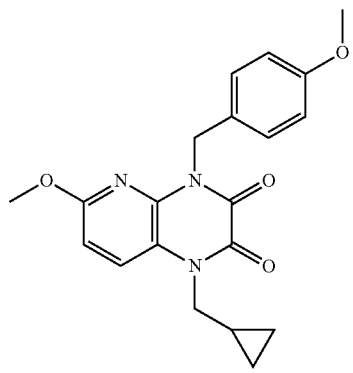

6-methoxy-4-[(4-methoxyphenyl)methyl]-1H-pyrido[2,3-b]pyrazine-2,3-dione (2.242 g, 7.156 mmol), cesium carbonate (6.99 g, 21.5 mmol), potassium iodide (123 mg, 0.718 mmol) and bromomethylcyclopropane (1.80 mL, 17.8 mmol) are combined in DMF (56 mL). The mixture is stirred under nitrogen at 80° C. overnight. The reaction is cooled to RT and combined with previous lot (156 mg scale reaction). The reaction is diluted with water and extracted with EtOAc. The organics are combined, washed with sat. aq. NaCl solution, dried over anhydrous MgSO$_4$, filtered and concentrated under reduced pressure. The residue is purified by flash chromatography on silica, eluting with 30-80% EtOAc in hexanes. The pure chromatography fractions are combined and concentrated under reduced pressure, drying under high vacuum to give the pink solid crude title compound (1.97 g). MS (m/z): 368 (M+H).

PREPARATION 18

Synthesis of 1-(cyclopropylmethyl)-6-methoxy-4H-pyrido[2,3-b]pyrazine-2,3-dione

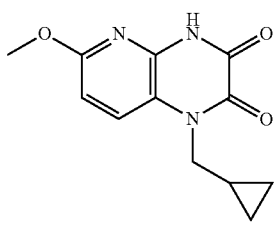 [SMILES: COc1ccc2c(n1)[nH]c(=O)c(=O)n2CC1CC1]

1-(Cyclopropylmethyl)-6-methoxy-4-[(4-methoxyphenyl)methyl]pyrido[2,3-b]pyrazine-2,3-dione (1.80 g, 4.90 mmol) is dissolved in TFA (10 mL) in a microwave vial sealed under nitrogen. The reaction is stirred at 120° C. for 1 hr. The reaction is concentrated under reduced pressure and concentrated from DCM once. The resulting green foam is dried under high vacuum to afford crude title compound (50 mass %), (2.4 g, 99%). MS (m/z): 248 (M+H).

Scheme 5

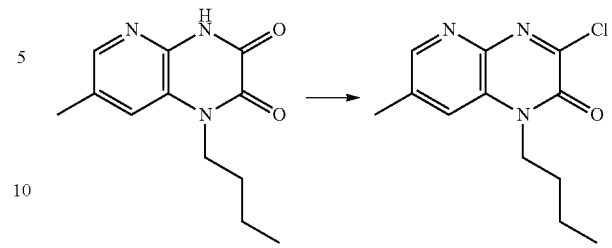

PREPARATION 19

Synthesis of 1-butyl-3-chloro-7-methyl-pyrido[2,3-b]pyrazine-2-one

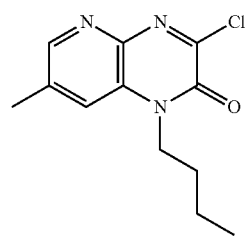 [SMILES: CCCCn1c(=O)c(Cl)nc2ncc(C)cc21]

Scheme 5: A stirred solution of 1-butyl-7-methyl-4H-pyrido[2,3-b]pyrazine-2,3-dione (2.198 g, 8.951 mmol) and DMF (0.05 mL, 0.6 mmol) in excess thionyl chloride (15 mL, 205.9 mmol) is heated at reflux. After 16 hr, the reaction mixture is cooled to RT, diluted with DCM and concentrated under reduced pressure. The crude material is suspended in toluene, sonicated, and concentrated under reduced pressure. The crude material is suspended in 10 mL cold DCM and collected by vacuum filtration. The material is air-dried for 1.5 hr to give a solid (1.655 g). The filtrate is concentrated under reduced pressure, suspended in DCM and placed in an ice bath overnight. The resulting suspension is filtered through a fine frit funnel and air-dried for 1 hr to give a solid (267 mg). The materials are combined to give the title compound, (1.922 g). MS (m/z): 252 (M+H).

Prepare the following compounds shown in Table 3 from 1-(cyclopropylmethyl)-6-methoxy-4H-pyrido[2,3-b]pyrazine-2,3-dione (for Prep. 20); from 7-bromo-1-butyl-4H-pyrido[2,3-b]pyrazine-2,3-dione (for Prep. No. 21); from 1-propyl-7-methyl-4H-pyrido[2,3-b]pyrazine-2,3-dione (for Prep. No. 22); and from 7-bromo-1-butyl-6-methyl-4H-pyrido[2,3-b]pyrazine-2,3-dione (for Prep. No. 23) in a manner essentially analogous to the method of Preparation 19 using a molar excess of thionyl chloride.

TABLE 3

| Prep. No. | Chemical Name | Structure | MS (m/z) |
| --- | --- | --- | --- |
| 20 | 3-Chloro-1-(cyclopropylmethyl)-6-methoxy-pyrido[2,3-b]pyrazine-2-one | 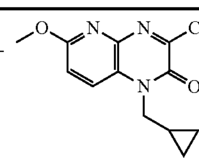 | 266/268 (M + H) |

TABLE 3-continued

| Prep. No. | Chemical Name | Structure | MS (m/z) |
|---|---|---|---|
| 21 | 7-Bromo-1-butyl-3-chloro-pyrido[2,3-b]pyrazine-2-one | 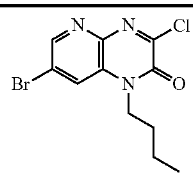 | 316/318 (M + H) |
| 22 | 3-Chloro-7-methyl-1-propyl-pyrido[2,3-b]pyrazine-2-one | 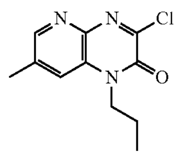 [SMILES: CCCn1c(=O)c(Cl)nc2ncc(C)cc21] | 238 (M + H) |
| 23 | 7-Bromo-1-butyl-3-chloro-6-methyl-pyrido[2,3-b]pyrazine-2-one | 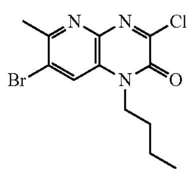 [SMILES: CCCCn1c(=O)c(Cl)nc2nc(C)c(Br)cc21] | 332 (M + H) |

Prepare the following compounds shown in Table 4 from rac-1-[2-methoxybutyl]-4H-pyrido[2,3-b]pyrazine-2,3-dione (for Prep. No. 25) and from 6-methyl-1,4-dihydropyrido[2,3-b]pyrazine-2,3-dione (for Prep. No. 26) in a manner essentially analogous to the method of Preparation 24 using a molar excess of hydrazine.

TABLE 4

| Prep. No. | Chemical Name | Structure | MS (m/z) |
|---|---|---|---|
| 25 | rac-3-Hydrazino-1-[2-methoxybutyl]pyrido[2,3-b]pyrazine-2-one | 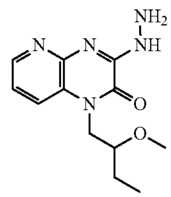 [SMILES: CCC(Cn1c(=O)c(NN)nc2ncccc21)OC] | 264 (M + H) |
| 26 | 3-Hydrazino-6-methyl-1H-pyrido[2,3-b]pyrazine-2-one | 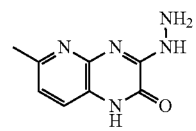 | 192 (M + H) |

Scheme 6

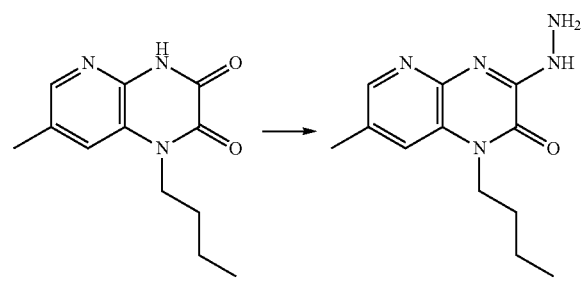

PREPARATION 24

Synthesis of 1-butyl-3-hydrazino-7-methyl-pyrido[2,3-b]pyrazine-2-one

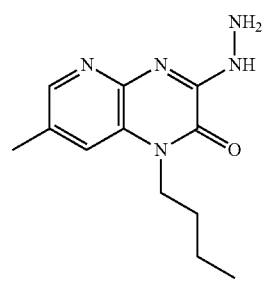

Scheme 6: A suspension of 1-butyl-7-methyl-4H-pyrido[2,3-b]pyrazine-2,3-dione (0.268 g, 1.15 mmol) in EtOH (7.0 mL) is degassed. Hydrazine (0.60 mL, 19 mmol) is added and the reaction is heated at 110° C. overnight. The reaction is concentrated and purified by flash chromatography on silica, eluting with DCM/MeOH. The pure chromatography fractions are combined and concentrated under reduced pressure to give the title compound as a dark yellow solid (0.226 g, 80%). MS (m/z): 248.0 (M+H).

Scheme 7

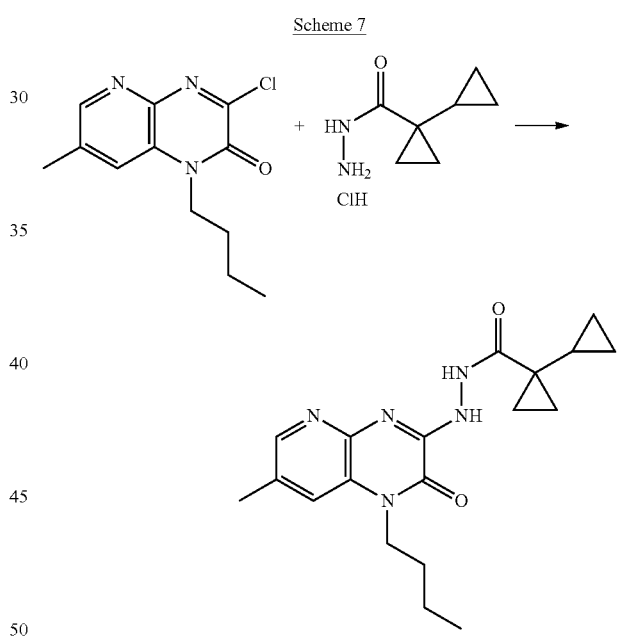

PREPARATION 27A

Synthesis of 1-cyclopropylcyclopropanecarbohydrazide hydrochloride

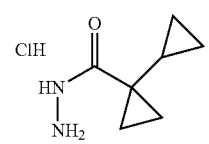

To a stirred solution of 1-cyclopropylcyclopropanecarboxylic acid (9.63 g, 76.3 mmol), and HATU (32.3 g, 83.2 mmol) in DMF (300 mL) is added tert-butyl carbazate (5.00 g, 37.8 mmol) followed by DIPEA (14.5 mL, 83.1 mmol), and the reaction is stirred at room temperature for 5 d. The reaction mixture is diluted with ethyl acetate, washed with 1.0 N hydrochloric acid, saturated NaHCO$_3$, and water. The organics are then dried over magnesium sulfate, filtered, and concentrated under reduced pressure. 1,4-Dioxane (50 mL) is added to the residue, hydrochloric acid (4 mol/L) in 1,4-dioxane (100 mL, 400 mmol) is added over 20 min and the reaction is stirred at room temperature for 1 h. The solution is filtered, the filter cake is washed with MTBE, and dried under reduced pressure to give the title compound, (8.01 g, 58.7%). MS (m/z): 141 (M+H)

PREPARATION 27B

Synthesis of 1-methylcyclopropanecarbohydrazide hydrochloride

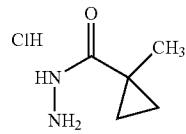

To a stirred solution of 1-methylcyclopropanecarboxylic acid (5.25 g, 52.4 mmol), DIPEA (7.3 mL, 42 mmol), and HATU (16.1 g, 41.5 mmol) in dichloromethane (200 mL) is added tert-butyl carbazate (5.00 g, 37.8 mmol), and the reaction is stirred at RT overnight. The reaction mixture is washed with 1.0 N hydrochloric acid, saturated NaHCO$_3$, and water. The organics are then dried over sodium sulfate, filtered, and concentrated under reduced pressure. The residue is cooled to 0° C. and dissolved in hydrochloric acid (4 mol/L) in 1,4-dioxane (75 mL, 300 mmol). After 5 min the reaction mixture became a white slurry, and was stirred at room temperature for 1 h. Additional hydrochloric acid (4 mol/L) in 1,4-dioxane (75 mL, 300 mmol) is added and the reaction is stirred overnight. The reaction is diluted with MTBE, filtered, the filter cake is washed with MTBE, and air dried to give crude title compound (6.42 g). 1H NMR (DMSO-d6) δ 10.64 (s, 1H), 10.23 (br s, 2H), 1.26 (s, 3H), 1.05-1.02 (m, 2H), 0.69-0.66 (m, 2H).

PREPARATION 27C

Synthesis of N'-(1-butyl-7-methyl-2-oxo-pyrido[2,3-b]pyrazine-3-yl)-1-cyclopropyl-cyclopropanecarbohydrazide

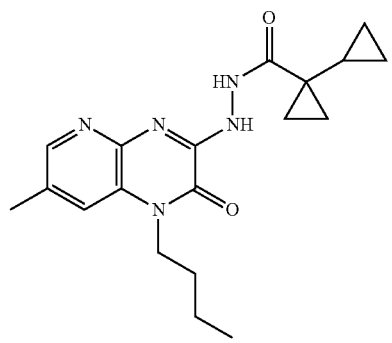 [SMILES: CCCCn1c(=O)c(NNC(=O)C2(C3CC3)CC2)nc2ncc(C)cc21]

Scheme 7: To an oven-dried RBF with 4 Å molecular sieves is added 1-butyl-3-chloro-7-methyl-pyrido[2,3-b]pyrazine-2-one (1.50 g, 6.0 mmol) and 1-cyclopropylcyclopropanecarbohydrazide hydrochloride (1.05 g, 5.94 mmol). The vessel is sealed, then evacuated and backfilled with nitrogen (3×). THF (40 mL) is added and the mixture is stirred at 50° C. After 1 hr, the reaction mixture is sonicated and stirred at 55° C. for 2 hr. The reaction mixture is cooled to RT and the resulting solids are collected via vacuum filtration, air-dried for 5 min, then dried under high vacuum for 1 hr to give the title compound (1.86 g). MS (m/z): 356 (M+H).

Prepare the following compounds shown in Table 5 from 7-bromo-1-butyl-3-chloro-pyrido[2,3-b]pyrazine-2-one (for Prep. No. 28); from 3-chloro-7-methyl-1-propyl-pyrido[2,3-b]pyrazine-2-one (for Prep. No. 29); from 7-bromo-1-butyl-3-chloro-pyrido[2,3-b]pyrazine-2-one and 1-methylcyclopropanecarbohydrazide hydrochloride (for Prep. No. 30), respectively, in a manner essentially analogous to the method of Preparation 27C.

TABLE 5

| Prep. No. | Chemical Name | Structure | MS (m/z) |
| --- | --- | --- | --- |
| 28 | N'-[(7-Bromo-1-butyl-2-oxo-4H-pyrido[2,3-b]pyrazine-3-ylidene)amino]-1-cyclopropyl-cyclopropanecarbohydrazide | 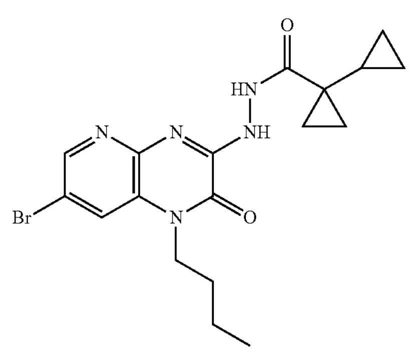 [SMILES: CCCCn1c(=O)c(NNC(=O)C2(C3CC3)CC2)nc2ncc(Br)cc21] | 420/422 (M + H) |

TABLE 5-continued

| Prep. No. | Chemical Name | Structure | MS (m/z) |
|---|---|---|---|
| 29 | N'-(1-propyl-7-methyl-2-oxo-pyrido[2,3-b]pyrazin-3-yl)-1-(cyclopropyl)cyclopropanecarbohydrazide | 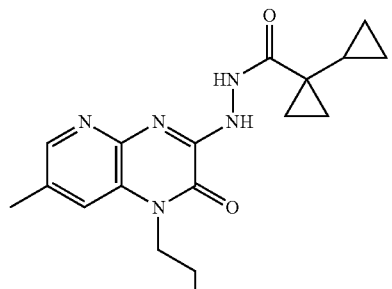 | 342 (M + H) |
| 30 | N'-(7-bromo-1-butyl-2-oxo-pyrido[2,3-b]pyrazin-3-yl)-1-methyl-cyclopropanecarbohydrazide | 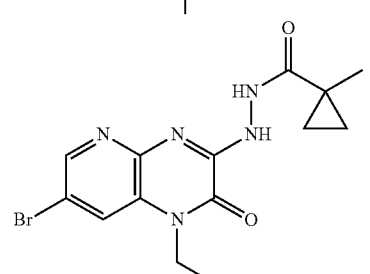 | 394/396 (M + H) |

Scheme 8

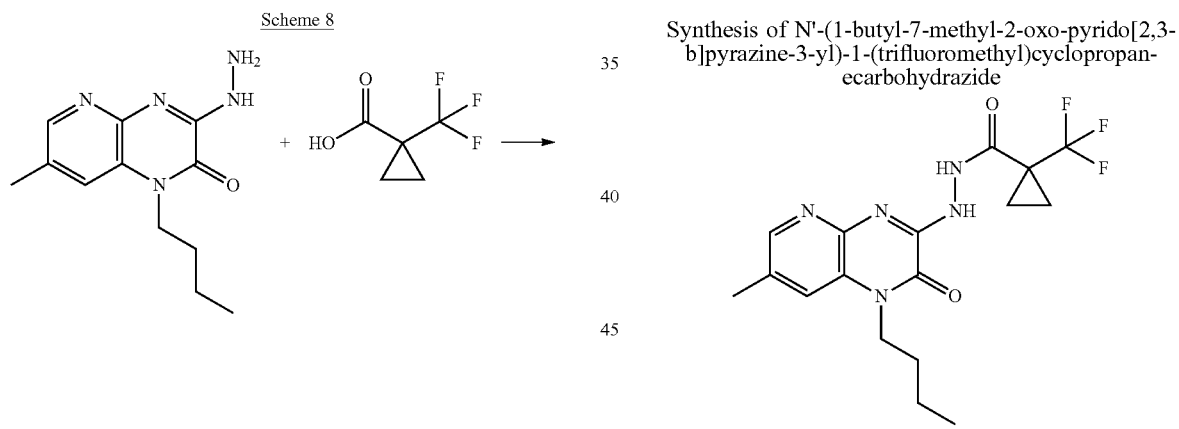

PREPARATION 31

Synthesis of N'-(1-butyl-7-methyl-2-oxo-pyrido[2,3-b]pyrazine-3-yl)-1-(trifluoromethyl)cyclopropanecarbohydrazide Scheme 8: TEA (0.44 mL, 3.2 mmol) is added to a mixture of 1-butyl-3-hydrazino-7-methyl-pyrido[2,3-b]pyrazine-2-one (0.224 g, 0.906 mmol), 1-(trifluoromethyl)cyclopropanecarboxylic acid (0.157 g, 1.01 mmol), HOBT (0.192 g, 1.39 mmol) and EDCI hydrochloride (0.258 g, 1.35 mmol) in THF (9.1 mL) and stirred at RT overnight. A solution is obtained by dilution with DCM and water before filtering through a pad of diatomaceous earth. The pad is washed with DCM and discarded. The filtrate is concentrated and purified by flash chromatography on silica, eluting with DCM/MeOH. The pure chromatography fractions are combined and concentrated under reduced pressure to give the title compound as a white solid (0.288 g). MS (m/z): 348.0 (M+H).

Prepare the following compounds shown in Table 6 from rac-3-hydrazino-1-[2-methoxybutyl]pyrido[2,3-b]pyrazine-2-one (for Prep. No. 32) and from 3-hydrazino-6-methyl-1H-pyrido[2,3-b]pyrazine-2-one (for Prep. No. 33) in a manner essentially analogous to the method of Preparation 31 using 1-cyclopropylcyclopropanecarboxylic acid.

TABLE 6

| Prep. No. | Chemical Name | Structure | MS (m/z) |
|---|---|---|---|
| 32 | rac-1-Cyclopropyl-N'-[1-[2-methoxybutyl]-2-oxo-pyrido[2,3-b]pyrazine-3-yl]cyclopropanecarbohydrazide | 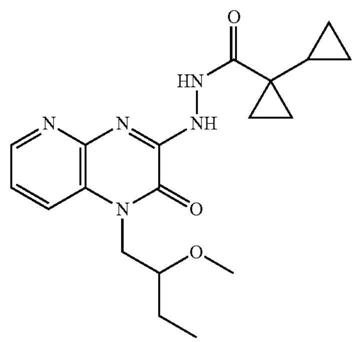 [SMILES: CCC(Cn1c(=O)c(NNC(=O)C2(C3CC3)CC2)nc2ncccc21)OC] | 372 (M + H) |
| 33 | 1-Cyclopropyl-N'-(6-methyl-2-oxo-1H-pyrido[2,3-b]pyrazine-3-yl)cyclopropanecarbohydrazide | 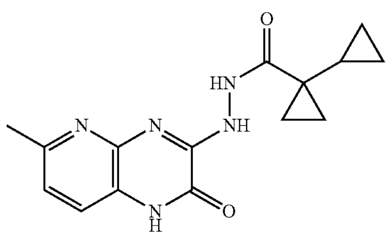 [SMILES: Cc1ccc2[nH]c(=O)c(NNC(=O)C3(C4CC4)CC3)nc2n1] | 300 (M + H) |

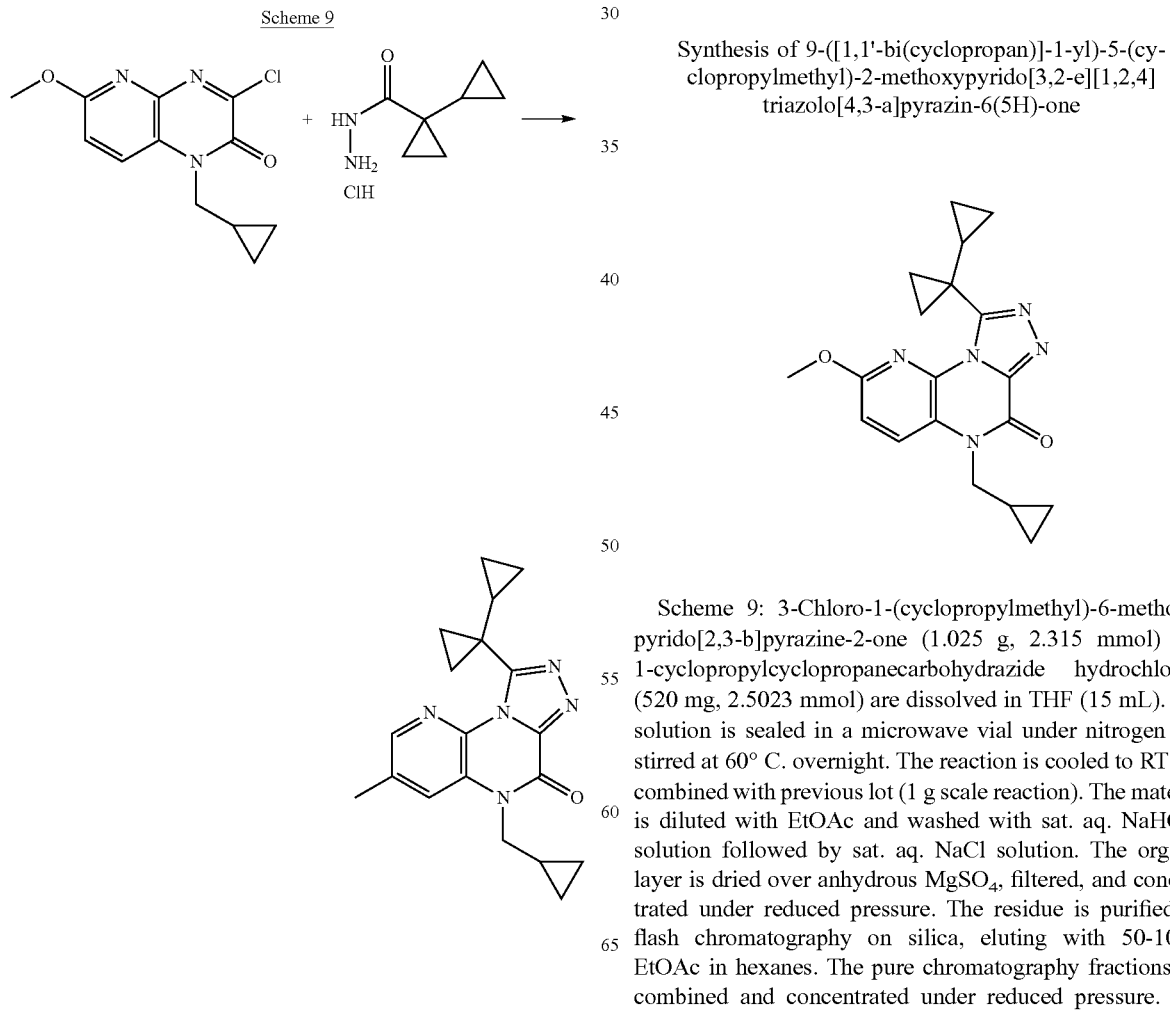

Scheme 9

PREPARATION 34

Synthesis of 9-([1,1'-bi(cyclopropan)]-1-yl)-5-(cyclopropylmethyl)-2-methoxypyrido[3,2-e][1,2,4]triazolo[4,3-a]pyrazin-6(5H)-one Scheme 9: 3-Chloro-1-(cyclopropylmethyl)-6-methoxy-pyrido[2,3-b]pyrazine-2-one (1.025 g, 2.315 mmol) and 1-cyclopropylcyclopropanecarbohydrazide hydrochloride (520 mg, 2.5023 mmol) are dissolved in THF (15 mL). The solution is sealed in a microwave vial under nitrogen and stirred at 60° C. overnight. The reaction is cooled to RT and combined with previous lot (1 g scale reaction). The material is diluted with EtOAc and washed with sat. aq. NaHCO₃ solution followed by sat. aq. NaCl solution. The organic layer is dried over anhydrous MgSO₄, filtered, and concentrated under reduced pressure. The residue is purified by flash chromatography on silica, eluting with 50-100% EtOAc in hexanes. The pure chromatography fractions are combined and concentrated under reduced pressure. The orange solid is dried under high vacuum to give the crude title compound (1.068 g). MS (m/z): 352 (M+H).

Prepare the following compound shown in Table 7 from 7-bromo-1-butyl-3-chloro-6-methyl-pyrido[2,3-b]pyrazine-2-one in a manner essentially analogous to the method of Preparation 34.

TABLE 7

| Prep. No. | Compound Name | Structure | MS (m/z) |
|---|---|---|---|
| 35 | 9-([1,1'-Bi(cyclopropan)]-1-yl)-3-bromo-5-butyl-2-methylpyrido[3,2-e][1,2,4]triazolo[4,3-a]pyrazin-6(5H)-one | 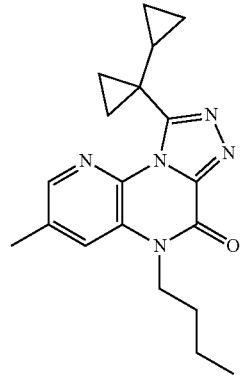 | 416/418 (M + H) |

Scheme 10

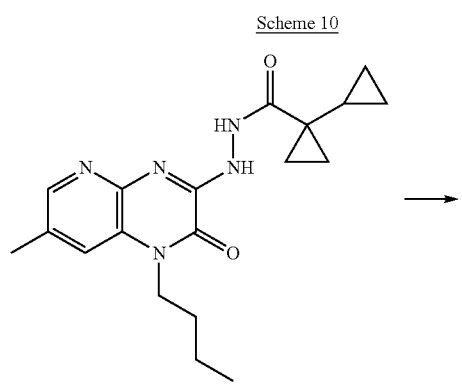

Example 1

Synthesis of 9-([1,1'-bi(cyclopropan)]-1-yl)-5-butyl-3-methylpyrido[3,2-e][1,2,4]triazolo[4,3-a]pyrazin-6 (5H)-one

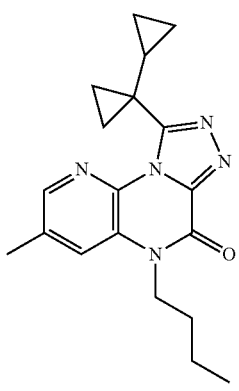

Scheme 10: To an oven-dried microwave vial with 4 Å molecular sieves is added N'-(1-butyl-7-methyl-2-oxo-pyrido[2,3-b]pyrazine-3-yl)-1-cyclopropyl-cyclopropanecarbohydrazide (1.83 g, 5.15 mmol). The vial is sealed, then evacuated and backfilled with nitrogen (3×). HMDS (17 mL, 81.2 mmol) is added followed by DBU (0.16 mL, 1.1 mmol) to give a suspension, which is heated at 125° C. with stirring. After 4 hr the reaction solution is transferred to a RBF with methanol and heated at 50° C. for 1 hr. The crude mixture is concentrated under reduced pressure and the resulting residue is partitioned between DCM and water. Layers are separated and the aqueous layer is extracted with DCM and 3:1 CHCl$_3$/IPA. The organics are combined, washed with sat. aq. NaCl solution, dried over anhydrous MgSO$_4$, filtered and concentrated under reduced pressure. The residue is dissolved in EtOH (17 mL) and water (100 mL) is added via addition funnel over 30 min. then cooled in an ice bath for 15 min. The solids are isolated by vacuum filtration, washed with water, air-dried for 15 min, and dried at 50° C. under vacuum overnight to give the title compound (1.14 g). MS (m/z): 338 (M+H).

Prepare the following compounds (preparations and examples) shown in Table 8 from N'-(1-butyl-7-methyl-2-oxo-pyrido[2,3-b]pyrazine-3-yl)-1-(trifluoromethyl)cyclopropanecarbohydrazide (for Example 2); from N-(7-bromo-1-butyl-2-oxo-pyrido[2,3-b]pyrazin-3-yl)-1-methyl-cyclopropanecarbohydrazide (for Prep. No. 36); from N-(1-propyl-7-methyl-2-oxo-pyrido[2,3-b]pyrazin-3-yl)-1-(cyclopropyl)cyclopropanecarbohydrazide (for Example 3); from N'-[(7-bromo-1-butyl-2-oxo-4H-pyrido[2,3-b]pyrazine-3-ylidene)amino]-1-cyclopropyl-cyclopropanecarbohydrazide (for Prep. No. 37); from 1-cyclopropyl-N'-(6-methyl-2-oxo-1H-pyrido[2,3-b]pyrazine-3-yl) cyclopropanecarbohydrazide (for Prep. No. 38): from rac-1-cyclopropyl-N'-[1-[2-methoxybutyl]-2-oxo-pyrido[2,3-b]pyrazine-3-yl]cyclopropanecarbohydrazide (for Example 4); in a manner essentially analogous to the method of Example 1.

TABLE 8

| Prep./Example No. | Compound Name | Structure | MS (m/z) |
|---|---|---|---|
| Example 2 | 5-Butyl-3-methyl-9-(1-(trifluoromethyl)cyclopropyl)pyrido[3,2-e][1,2,4]triazolo[4,3-a]pyrazin-6(5H)-one | 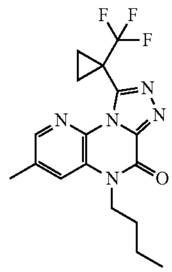 [SMILES: CCCCn1c(=O)c2nnc(C3(C(F)(F)F)CC3)n2c2ncc(C)cc21] | 366 (M + H) |
| Prep. 36 | 3-Bromo-5-butyl-9-(1-methylcyclopropyl)pyrido[3,2-e][1,2,4]triazolo[4,3-a]pyrazine-6(5H)-one | 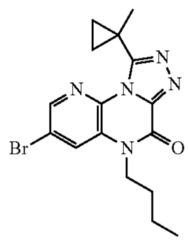 [SMILES: CCCCn1c(=O)c2nnc(C3(C)CC3)n2c2ncc(Br)cc21] | 376/378 (M + H) |
| Example 3 | 9-([1,1'-Bi(cyclopropan)]-1-yl)-3-methyl-5-propylpyrido[3,2-e][1,2,4]triazolo[4,3-a]pyrazin-6(5H)-one | 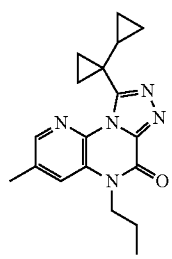 [SMILES: CCCn1c(=O)c2nnc(C3(C4CC4)CC3)n2c2ncc(C)cc21] | 324 (M + H) |
| Prep. 37 | 9-([1,1'-Bi(cyclopropan)]-1-yl)-3-bromo-5-butylpyrido[3,2-e][1,2,4]triazolo[4,3-a]pyrazin-6(5H)-one | 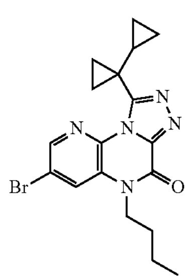 [SMILES: CCCCn1c(=O)c2nnc(C3(C4CC4)CC3)n2c2ncc(Br)cc21] | 402/404 (M + H) |
| Prep. 38 | 9-([1,1'-Bi(cyclopropan)]-1-yl)-2-methylpyrido[3,2-e][1,2,4]triazolo[4,3-a]pyrazin-6(5H)-one | 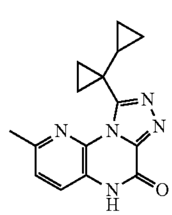 [SMILES: Cc1ccc2[nH]c(=O)c3nnc(C4(C5CC5)CC4)n3c2n1] | 282 (M + H) |
| Example 4 | rac-9-([1,1'-Bi(cyclopropan)]-1-yl)-5-(2-methoxybutyl)-pyrido[3,2-e][1,2,4]triazolo[4,3-a]pyrazin-6(5H)-one | 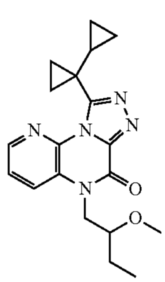 [SMILES: CCC(Cn1c(=O)c2nnc(C3(C4CC4)CC3)n2c2ncccc21)OC] | 354 (M + H) |

Example 4a

Synthesis of 9-([1,1'-bi(cyclopropan)]-1-yl)-5-(2-methoxybutyl)pyrido[3,2-e][1,2,4]triazolo[4,3-a]pyrazin-6(5H)-one (isomer 1)

Isomer 1

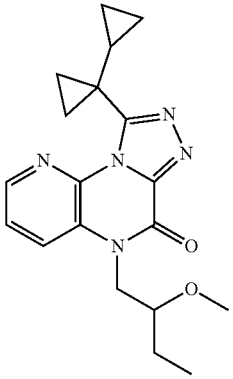

rac-9-([1,1'-Bi(cyclopropan)]-1-yl)-5-(2-methoxybutyl)pyrido[3,2-e][1,2,4]triazolo[4,3-a]pyrazin-6(5H)-one (0.148, 0.42 mmol) is dissolved for chiral separation using MeOH (2.0 mL), DCM (1.0 mL), then rinsed with DCM (2.0 mL) and MeOH (1.0 mL). The 6 mL feed solution is filtered and injected in 1.0 mL increments for a total of 6 total injections. The column is a (S,S) Whelk-01 10 um, with a flow rate of 80 mL/minute, 40% MeOH/60% $CO_2$ mobile phase to give isomer 1 as the title compound (57 mg; first eluting isomer). (S,S) Whelk-01 10 um, 40% MeOH/$CO_2$, 5 mL/min, 225 nm: TR=2.22 min, >99% ee. MS (m/z): 354.2 (M+H); $[\alpha]_D^{20}$ −8.1° (c 0.20, methanol).

Example 4b

Synthesis of 9-([1,1'-bi(cyclopropan)]-1-yl)-5-(2-methoxybutyl)pyrido[3,2-e][1,2,4]triazolo[4,3-a]pyrazin-6(5H)-one (isomer 2)

Isomer 2

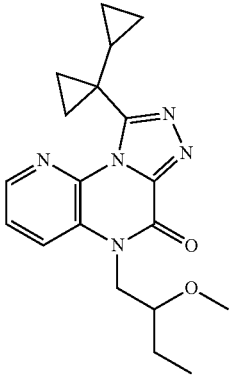

The compound of Example 6 is isolated essentially by the method of Example 5 to give isomer 2 as the title compound (61 mg; second eluting isomer). (S,S) Whelk-01 10 um, 40% MeOH/CO2, 5 mL/min, 225 nm: TR=3.08 min, >99% ee. MS (m/z): 354.2 (M+H); $[\alpha]_D^{20}$ +7.1° (c 0.20, methanol).

Example 5

Synthesis of 9-([1,1'-bi(cylopropan)]-1-yl)-5-(cyclopropylmethyl)-2-hydroxypyrido[3,2-e][1,2,4]triazolo[4,3-a]pyrazin-6(5H)-one

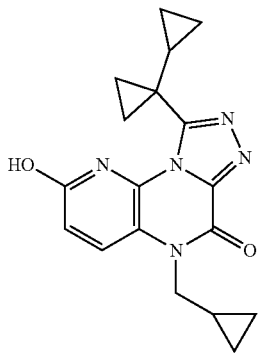 [SMILES: O=c1c2nnc(C3(C4CC4)CC3)n2c2nc(O)ccc2n1CC1CC1]

9-([1,1'-Bi(cyclopropan)]-1-yl)-5-(cyclopropylmethyl)-2-methoxypyrido[3,2-e][1,2,4]triazolo[4,3-a]pyrazin-6(5H)-one (460 mg, 1.309 mmol), sodium ethanethiolate (487 mg, 5.210 mmol) and 1-methyl-2-pyrrolidinone (5 mL, 51.90 mmol) are combined and sealed in a microwave vial under nitrogen. The reaction is irradiated in the microwave at 200° C. for 12 hr. The reaction mixture is combined with the reaction mixture from previous lot (30 mg scale reaction) and diluted with water. The aqueous layer is acidified to pH~3 with 1N aq. HCl, and extracted with EtOAc. The organics are combined, washed with sat. aq. NaCl solution, dried over anhydrous MgSO$_4$, filtered, and concentrated under reduced pressure. The residue is purified by reverse phase flash chromatography on C18 eluting with 10-100% ACN in water (10 mM (NH$_4$)HCO$_3$ w/5% MeOH). The pure chromatography fractions are combined and concentrated under reduced pressure to aqueous, extracted with DCM, washed with sat. aq. NaCl solution, dried over anhydrous MgSO$_4$, filtered and concentrated under reduced pressure. The off-white solid is dried under vacuum give the title compound (84 mg). MS (m/z): 338 (M+H).

Example 6

Synthesis of 5-butyl-3-methyl-9-(1-methylcyclopropyl)pyrido[3,2-e][1,2,4]triazolo[4,3-a]pyrazin-6(5H)-one

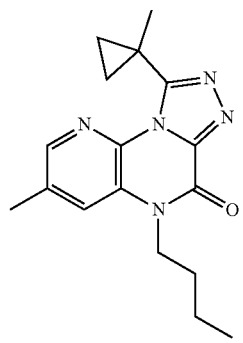 [SMILES: CCCCn1c(=O)c2nnc(C3(C)CC3)n2c2ncc(C)cc21]

[1,1'-Bis(diphenylphosphino)ferrocene]dichloropalladium(II) (9 mg, 0.012 mmol) is added to a solution of 3-bromo-5-butyl-9-(1-methylcyclopropyl)pyrido[3,2-e][1,2,4]triazolo[4,3-a]pyrazin-6(5H)-one (90 mg, 0.2392 mmol) in THF (0.6 mL, 7 mmol) in a microwave vial. After stirring for 10 min, methylzinc chloride (350 µL, 0.7 mmol, 2 mol/L in THF) is added and the vessel is evacuated and purged with nitrogen. The reaction mixture is stirred at 80° C. for 2 hr, cooled to RT and combined with an additional run (37 mg scale reaction) diluting with sat. aq. NH$_4$Cl solution. The aqueous layer is extracted with EtOAc, the organics are combined, washed with sat. aq. NaCl solution, dried over anhydrous Na$_2$SO$_4$, filtered and concentrated under reduced pressure. Purification by flash chromatography on silica, eluting with 0-100% EtOAc in hexanes to give the title compound (75 mg). MS (m/z): 312 (M+H).

Prepare the following compound shown in Table 9 from 9-([1,1'-bi(cyclopropan)]-1-yl)-3-bromo-5-butyl-2-methylpyrido[3,2-e][1,2,4]triazolo[4,3-a]pyrazin-6(5H)-one in a manner essentially analogous to the method of Example 7.

TABLE 9

| Example No. | Compound Name | Structure | MS (m/z) |
|---|---|---|---|
| 7 | 9-([1,1'-Bi(cyclopropan)]-1-yl)-5-butyl-2,3-dimethylpyrido[3,2-e][1,2,4]triazolo[4,3-a]pyrazin-6(5H)-one | 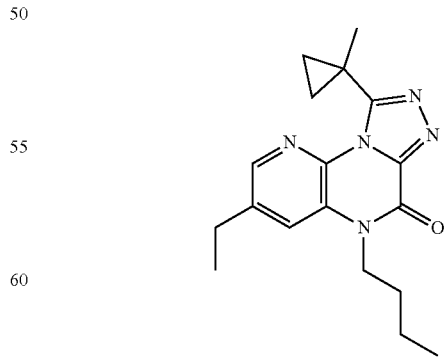 | 352 (M + H) |

Example 8

Synthesis of 5-butyl-3-ethyl-9-(1-methylcyclopropyl)pyrido[3,2-e][1,2,4]triazolo[4,3-a]pyrazin-6(5H)-one 3-Bromo-5-butyl-9-(1-methylcyclopropyl)pyrido[3,2-e][1,2,4]triazolo[4,3-c]pyrazin-6(5H)-one (89 mg, 0.2366 mmol), 1,1'-bis(diphenylphosphino)ferrocene-palladium(II)

dichloride dichloromethane complex (11 mg, 0.0132 mmol), and 1,4-dioxane (1.0 mL) are combined in a microwave vial. The vial is sealed under nitrogen and diethylzinc (0.50 mL, 0.50 mmol, 1 mol/L in hexanes) is added and stirred at RT overnight. The reaction mixture is quenched with sat. aq. NaCl solution and combined with an additional run (23 mg scale reaction). The mixture is diluted with EtOAc and water, the layers are separated and the aqueous layer is extracted with EtOAc followed by 3:1 CHCl$_3$/IPA. The organics are combined, washed with sat. aq. NaCl solution, dried over anhydrous MgSO$_4$, filtered, and concentrated under reduced pressure. The residue is purified by flash chromatography on silica, eluting with 0-7% MeOH in DCM to give a crude material which is further purified by reverse phase flash chromatography on C18, eluting in 10-100% ACN in water (10 mM (NH$_4$)HCO$_3$ w/5% MeOH to give the title compound (60 mg, 60%). MS (m/z): 326 (M+H).

Prepare the following compound shown in Table 10 from 9-([1,1'-bi(cyclopropan)]-1-yl)-3-bromo-5-butylpyrido[3,2-e][1,2,4]triazolo[4,3-a]pyrazin-6(5H)-one in a manner essentially analogous to the method of Example 9.

TABLE 10

| Example No. | Compound Name | Structure | MS (m/z) |
|---|---|---|---|
| 9 | 9-([1,1'-Bi(cyclopropan)]-1-yl)-5-butyl-3-ethylpyrido[3,2-e][1,2,4]triazolo[4,3-a]pyrazin-6(5H)-one | 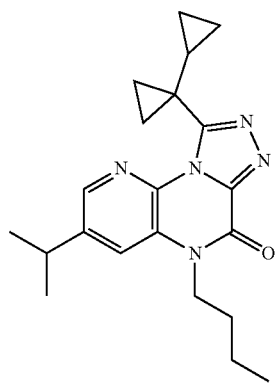 | 324 (M + H) |

Example 10

Synthesis of 9-([1,1'-bi(cyclopropan)]-1-yl)-5-butyl-3-isopropylpyrido[3,2-e][1,2,4]triazolo[4,3-a]pyrazin-6(5H)-one Pd-PEPPSI-IHeptCl (3 mg, 0.003071 mmol) and 9-([1,1'-bi(cyclopropan)]-1-yl)-3-bromo-5-butylpyrido[3,2-e][1,2,4]triazolo[4,3-a]pyrazin-6(5H)-one (100 mg, 0.2486 mmol) are added to a RBF, purged and backfilled with nitrogen. Toluene (2.5 mL) is added and the solution is cooled to 0° C. 2-Propylzinc bromide (600 μL, 0.3 mmol, 0.5 mol/L in THF) is added and the reaction is brought to RT. Additional Pd-PEPPSI-IHeptCl (3 mg, 0.003071 mmol, 100 mass %) is added, the vessel is evacuated, purged with nitrogen, and stirred at RT overnight. The reaction is quenched with sat. aq. NH$_4$Cl solution and diluted with DCM. The phases are separated and the aqueous is extracted with DCM. The organics are combined, dried over anhydrous Na$_2$SO$_4$, filtered and concentrated under reduced pressure. The residue is purified by flash chromatography on silica, eluting in 0-100% EtOAc in hexanes to give the title compound (30 mg, 33%). MS (m/z): 366 (M+H).

Scheme 11

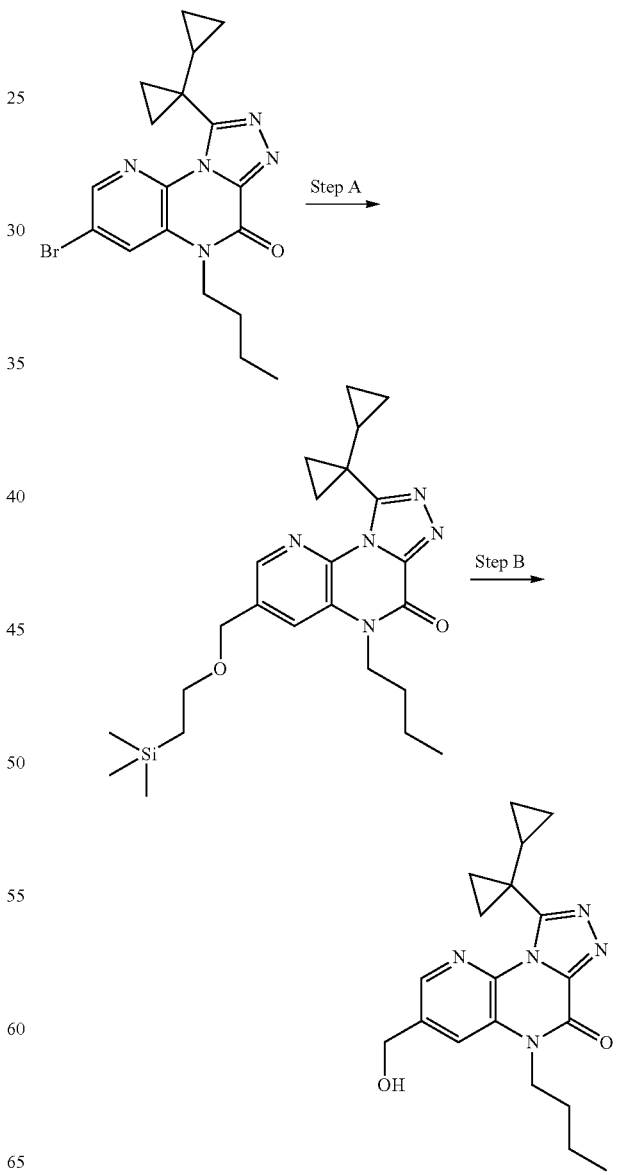

Example 11

Synthesis of 9-([1,1'-bi(cyclopropan)]-1-yl)-5-butyl-3-((2-(trimethylsilyl)ethoxy)methyl)pyrido[3,2-e][1,2,4]triazolo[4,3-a]pyrazin-6(5H)-one

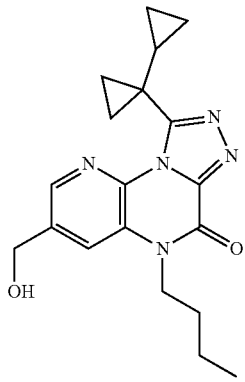 [SMILES: CCCCn1c(=O)c2nnc(C3(C4CC4)CC3)n2c2ncc(CO)cc21]

Scheme 11, Step A: 9-([1,1'-bi(cyclopropan)]-1-yl)-3-bromo-5-butylpyrido[3,2-e][1,2,4]triazolo[4,3-a]pyrazin-6(5H)-one (597 mg, 1.484 mmol), potassium trifluoro(2-trimethylsilylethoxymethyl)boranuide (430 mg, 1.8054 mmol), methanesulfonato(2-dicyclohexylphosphino-2',6'-di-i-propoxy-1,1'-biphenyl)(2'-amino-1,1'-biphenyl-2-yl)palladium(II) (133 mg, 0.154249 mmol), 2-dicyclohexylphosphino-2'6'-diisopropoxy-1,1'-biphenyl (74 mg, 0.150651 mmol), and cesium carbonate (1.48 g, 4.54 mmol) are combined in a microwave vial. The vial is sealed under nitrogen, a solution of 1,4-dioxane (5.0 mL) and water (0.50 mL) is added and the reaction mixture is stirred at 100° C. overnight. Additional 2-dicyclohexylphosphino-2'6'-diisopropoxy-1,1'-biphenyl (32 mg) and methanesulfonato(2-dicyclohexylphosphino-2',6'-di-i-propoxy-1,1'-biphenyl)(2'-amino-1,1'-biphenyl-2-yl)palladium(II) (65 mg) are added and the reaction is stirred at 105° C. for 2 days. The reaction mixture is combined with an additional run (100 mg scale reaction) and the mixture is diluted with EtOAc and washed with water followed by sat. aq. NaCl solution. The organic layer is dried over anhydrous Na$_2$SO$_4$, decanted, and concentrated under reduced pressure. The residue is purified by flash chromatography on silica, eluting with 40-65% EtOAc in hexanes to give 9-([1,1'-Bi(cyclopropan)]-1-yl)-5-butyl-3-((2-(trimethylsilyl)ethoxy)methyl)pyrido[3,2-e][1,2,4]triazolo[4,3-a]pyrazin-6(5H)-one (370 mg). MS (m/z): 454.

Scheme 11, Step B: 9-([1,1'-Bi(cyclopropan)]-1-yl)-5-butyl-3-((2-(trimethylsilyl)ethoxy)methyl)pyrido[3,2-e][1,2,4]triazolo[4,3-a]pyrazin-6(5H)-one (370 mg, 0.5710 mmol) and DCM (3 mL) are combined in a microwave vial. The vial is sealed under nitrogen and cooled to 0° C. in an ice bath. Boron trifluoride diethyl etherate (0.36 mL, 2.8 mmol) is added dropwise and the reaction mixture is allowed to warm to RT overnight. The reaction is quenched with sat. aq. NaHCO$_3$ solution and diluted with DCM. The organics are washed with sat. aq. NaCl solution, dried over anhydrous MgSO$_4$, filtered, and concentrated under reduced pressure. The residue is purified by flash chromatography on silica, eluting with 50-100% EtOAc in hexanes to give a residue. The residue is purified by reverse phase flash chromatography on C18, eluting in 10-100% ACN in water to give the title compound (49 mg). MS (m/z): 354 (M+H).

Prepare the following compound as shown in Table 11 from 3-bromo-5-butyl-9-(1-methylcyclopropyl)pyrido[3,2-e][1,2,4]triazolo[4,3-a]pyrazin-6(5H)-one in a manner essentially analogous to the method of Example 12.

TABLE 11

| Example No. | Chemical Name | Structure | MS (m/z) |
|---|---|---|---|
| 12 | 5-Butyl-3-(hydroxymethyl)-9-(1-methylcyclopropyl)pyrido[3,2-e][1,2,4]triazolo[4,3-a]pyrazin-6(5H)-one | 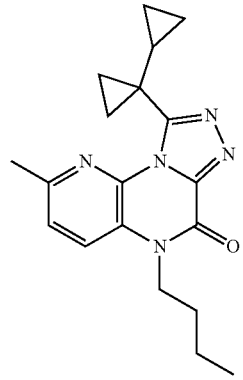 | 328 (M + H) |

Example 13

Synthesis of 9-([1,1'-bi(cyclopropan)]-1-yl)-5-butyl-2-methylpyrido[3,2-e][1,2,4]triazolo[4,3-a]pyrazin-6(5H)-one Lithium bis(trimethylsilyl)amide (2.1 mL, 2.1 mmol, 1 mol/L in MTBE) is added to 1-([1,1'-bi(cyclopropan)]-1-yl)-7-methylpyrido[2,3-e][1,2,4]triazolo[4,3-a]pyrazin-4(5H)-one (199 mg, 0.7074 mmol) in DMF (7 mL) and the reaction is stirred at RT for 1 hr. 1-Bromobutane (380 µL, 3.539 mmol) and potassium iodide (12 mg, 0.07229 mmol) are added and the reaction is stirred at 50° C. for 3 d. The reaction is cooled to RT and combined with two additional runs (50 mg scale each). The solution is extracted with 3:1 CHCl$_3$/IPA, the organic layer is dried over anhydrous MgSO$_4$, filtered, and concentrated under reduced pressure. The residue is dissolved in EtOH and added to water and the resulting precipitate is collected by filtration. The collected solids are purified by reverse phase flash chromatography on C18, eluting in 15-100% ACN in water to give the title compound (145 mg). MS (m/z): 338 (M+H).

Generation of PDE Proteins

The nucleotide sequences encoding full-length human PDE1A (NP_001003683.1) and PDE1C (NP_005011.1) are inserted into pFastBac1 (Invitrogen) vector with an N-terminal HIS tag. The nucleotide sequences encoding full-length human PDE4D (NP_006194.2) and catalytic domain (residue 641-1141) of PDE3A (NP_000912.3) are inserted into pFastBac1 (Invitrogen) vector with a C-terminal HIS tag. The nucleotide sequences encoding full-length human PDE6A (NP_000431.2) and PDE6B (AAH00249.1) are inserted into pFastBacDual (Invitrogen) vector with an N-terminal HIS tag and N-terminal Flag tag, respectively, for production of PDE6A/6B dimer. Baculovirus generation and protein expression in Sf9 cells are carried out according to the protocol of Bac-to-Bac Baculovirus Expression system (Invitrogen). The nucleotide sequence encoding full-length human PDE1B (NP_000915.1) is inserted into pIEX4 (Novagen) with a C-terminal HIS tag, and both protein productions in Sf9 cells are carried out according to the vendor's protocol (Novagen). The His tagged PDE proteins are purified using Ni-NTA agarose (Qiagen) followed by size exclusion chromatography on a SUPERDEX® 200 column (GE Healthcare) in storage buffer (20 mM Tris-HCl, pH7.5, 150 mM NaCl, 10% Glycerol). The Flag tagged PDE proteins including PDE6A/6B are purified using anti-Flag M2-agarose (Sigma), after purification through NiNTA column chromatography and eluted in storage buffer (50 mM Tris-HCl, pH7.5, 150 mM NaCl, 10% Glycerol, 0.1 mg/ml Flag peptide). All purified proteins are stored at −80° C. in small aliquots.

Phosphodiesterase Enzyme Assays

All 3',5' cyclic nucleotide phosphodiesterase (PDE) enzyme activities are measured with a radiometric enzyme assay based on SPA detection system (scintillation proximity assay). Compounds to be tested are diluted in pure dimethyl sulfoxide (DMSO) using ten point concentration response curves. Maximal compound concentration in the reaction mixture is either 10 or 100 µM. Compounds at the appropriate concentration are pre-incubated with either of the PDE enzymes for 30 minutes before the reaction is started by the addition of substrate. Reactions are allowed to proceed for 60 minutes at room temperature. Next, reactions are stopped by addition of SPA beads. Samples are read 12 hours later in a MICROBETA™ TRILUX® Counter. "$IC_{50}$" refers to the concentration of the compound that produces 50% of the maximal inhibitory response possible for that compound. $IC_{50}$ values are calculated by plotting the normalized data vs. log [compound] and fitting the data using a four parameter logistic equation.

$Ca^{2+}$-Calmodulin Dependent PDE Enzyme Assays

PDE1B, PDE1A, and PDE1C are cloned and purified following standard protein generation procedures. The assay buffer is prepared to give a final concentration in the assay of 50 mM Tris-HCl, 50 mM $MgCl_2$, 4 mM $CaCl_2$, 0.1% Bovine serum albumin and 6 U/ml Calmodulin in water, at pH 7.5. The final enzyme concentration is 0.25, 0.074 and 0.0012 nM, for PDE1A, PDE1B and PDE1C respectively. The reactions are started by addition of the substrate, [$^3$H] cAMP, to give a final concentration of 47 nM.

TABLE 12

In vitro potency of Examples 1 to 13 against human PDE1A, PDE1B, and PDE1C.

| Example | PDE 1A $IC_{50}$ (nM) | PDE 1B $IC_{50}$ (nM) | PDE 1C $IC_{50}$ (nM) |
|---|---|---|---|
| 1 | 0.366 ± 0.765 (n = 4) | 0.406 ± 1.08 (n = 3) | <0.508 (n = 3) |
| 2 | 8.62 ± 2.53 (n = 2) | 12.1 ± 1.06 (n = 2) | 1.62 ± 0.231 (n = 2) |
| 3 | 2.59 ± 1.69 (n = 2) | 3.41 ± 1.52 (n = 2) | 2.77 ± 0.636 (n = 2) |
| 4 | 13.9 ± 2.06 (n = 2) | 33.5 ± 6.26 (n = 2) | 0.609 ± 0.128 (n = 2) |
| 4a | 26.8 | 40.1 | 1.49 |
| 4b | 15.1 ± 2.84 (n = 2) | 25.8 ± 0.614 (n = 2) | 1.46 ± 0.642 (n = 2) |
| 5 | 2.75 ± 2.11 (n = 3) | 2.41 ± 0.846 (n = 3) | 0.931 ± 0.132 (n = 3) |
| 6 | 11.6 ± 7.55 (n = 2) | 15.4 ± 0.0529 (n = 2) | 2.57 ± 0.544 (n = 2) |
| 7 | 0.343 ± 0.765 (n = 2) | 0.400 ± 0.867 (n = 2) | <0.5 (n = 2) |
| 8 | 8.01 ± 3.55 (n = 2) | 9.34 ± 4.33 (n = 2) | 2.14 ± 0.997 (n = 2) |
| 9 | 0.214 ± 0.291 (n = 2) | 0.419 ± 0.713 (n = 2) | <0.5 (n = 2) |
| 10 | 0.260 ± 0.589 (n = 2) | 0.396 ± 0.749 (n = 2) | <0.5 (n = 2) |
| 11 | 0.996 ± 1.79 (n = 2) | 0.928 ± 1.56 (n = 2) | <0.5 (n = 2) |
| 12 | 23.0 ± 3.62 (n = 2) | 17.4 ± 10.0 (n = 2) | 4.02 ± 0.167 (n = 2) |
| 13 | 0.816 ± 0.198 (n = 3) | 1.13 ± 0.254 (n = 3) | <0.5 (n = 3) |

The data in Table 12 demonstrate that the compounds of Examples 1-13 inhibit human PDE1A, PDE1B, and PDE1C enzyme activity in vitro.

PDE Enzyme Assays Using [$^3$H]cAMP as Substrate

The following phosphodiesterase activities are measured using [$^3$H]cAMP as reaction substrate: human PDE3A (catalytic domain) and human PDE4D. Both enzymes are cloned and purified following standard procedures. The assay buffer is prepared to give a final concentration in the assay of 50 mM Tris-HCl, 8.3 mM $MgCl_2$, 1.7 mM ethylenediaminetetraacetic acid (EDTA) and 0.1% Bovine serum albumin at pH 7.5. Final enzyme concentrations are 0.008 and 0.021 nM for PDE3A and PDE4D, respectively. Reactions are started by addition of the substrate, [$^3$H]cAMP, to give a final concentration of 47 nM.

TABLE 13

In vitro potency of Examples 1-13against human PDE3A (catalytic domain) andPDE4D.

| Example | PDE 3A $IC_{50}$ (µM) | PDE 4D $IC_{50}$ (µM) |
|---|---|---|
| 1 | >50 (n = 3) | 1.59 ± 0.217 (n = 2) |
| 2 | >100 | 26 |
| 3 | >100 | 2.12 |
| 4 | >100 | 33.6 |
| 4a | >100 | >100 |
| 4b | >100 | >100 |
| 5 | 22.9 ± 1.14 (n = 2) | 14.7 ± 8.24 (n = 3) |
| 6 | >100 | 6.01 |
| 7 | 71.2 | 3.02 |
| 8 | >100 | 0.957 |
| 9 | >100 | 0.675 |

TABLE 13-continued

In vitro potency of Examples 1-13 against human PDE3A (catalytic domain) and PDE4D.

| Example | PDE 3A IC$_{50}$ (μM) | PDE 4D IC$_{50}$ (μM) |
|---|---|---|
| 10 | >100 | 0.972 |
| 11 | >100 | 5.56 |
| 12 | ≥93.4 (n = 3) | 5.13 ± 2.14 (n = 3) |
| 13 | 19.2 | 2.09 |

PDE Enzyme Assays Using [³H]cGMP as Substrate

The following phosphodiesterase activities are measured using [³H]cGMP as reaction substrate: human PDE6A/6B. The catalytic active form of human PDE6 is a dimer composed of a α (human PDE6A) and β subunits (human PDE6B). The dimer of human PDE6A/6B is produced by the coexpression and purification strategy, using two purification steps, i.e., NiNTA and anti-FLAG Sepharose chromatography. The assay buffer is prepared to give a final concentration in the assay of 50 mM Tris-HCl, 8.3 mM MgCl$_2$, 1.7 mM EDTA and 0.1% Bovine serum albumin at pH 7.5. The final enzyme concentration is 5 nM. The reactions are started by addition of the substrate, [³H]cGMP, to give a final concentration of 80 nM.

TABLE 14

In vitro potency of Examples 1 to 13 against PDE6AB.

| Example | PDE 6AB IC$_{50}$ (μM) |
|---|---|
| 1 | ≥3.45 (n = 2) |
| 2 | >10.0 |
| 3 | >10.0 |
| 4 | >10.0 |
| 4a | >10.0 |
| 4b | >10.0 |
| 5 | >10.0 (n = 3) |
| 6 | 9.59 |
| 7 | 1.2 |
| 8 | 3.29 |
| 9 | 0.982 |
| 10 | 0.611 |
| 11 | 3.85 |
| 12 | 3.06 ± 1.45 (n = 2) |
| 13 | 2.99 |

The data in Tables 12, 13, and 14 demonstrate that the compounds of Examples 1-13 are selective inhibitors of human PDE1A, PDE1B, and PDE1C relative to human PDE3A, PDE4D, and PDE6AB in vitro.

We claim:

1. A compound of the formula:

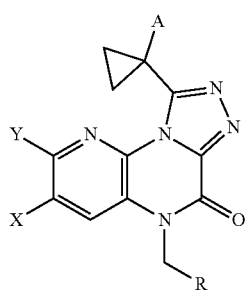

wherein X is H or C1-C3 alkyl optionally substituted with hydroxyl;
Y is H, hydroxy, or methyl;
R is ethyl, n-propyl, cyclopropyl, or

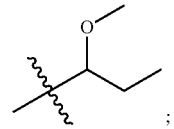 [SMILES: *C(CC)OC]

and
A is methyl, cyclopropyl or trifluoromethyl;
or a pharmaceutically acceptable salt thereof;
with the proviso that when X and Y are both H and R is n-propyl, then A is other than methyl.

2. The compound or salt according to claim 1 wherein X is methyl.

3. The compound or salt according to claim 1 wherein Y is H.

4. The compound or salt according to claim 1 wherein R is n-propyl.

5. The compound or salt according to claim 1 wherein A is cyclopropyl.

6. The compound according to claim 1 wherein the compound is in the free base form.

7. The compound or salt according to claim 1 wherein the compound is of the formula:

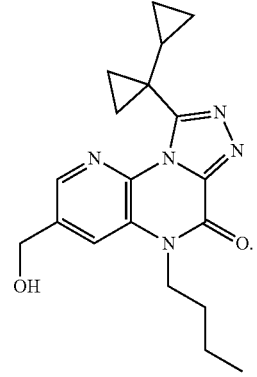 [SMILES: CCCCn1c(=O)c2nnc(C3(C4CC4)CC3)n2c2ncc(CO)cc21]

8. The compound according to claim 1 wherein the compound is of the formula:

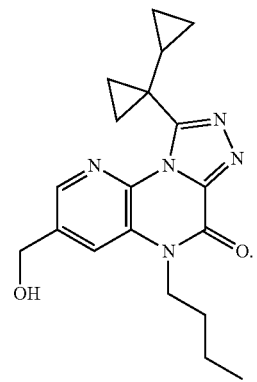 [SMILES: CCCCn1c(=O)c2nnc(C3(C4CC4)CC3)n2c2ncc(CO)cc21]

9. The compound or salt according to claim 1 wherein the compound is of the formula:

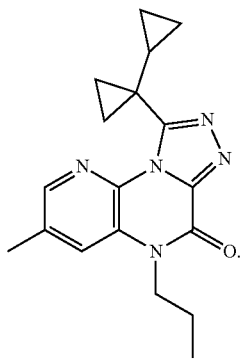 [SMILES: CCCn1c(=O)c2nnc(C3(C4CC4)CC3)n2c2ncc(C)cc21]

10. The compound according to claim 1 wherein the compound is of the formula:

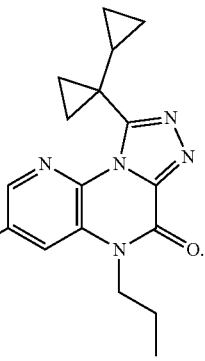

11. A pharmaceutical composition, comprising a compound or a pharmaceutically-acceptable salt thereof according to claim 1, with one or more pharmaceutically acceptable carriers, diluents, or excipients.

12. A process for preparing a pharmaceutical composition, comprising admixing a compound according to claim 1, or a pharmaceutically-acceptable salt thereof, with one or more pharmaceutically acceptable carriers, diluents, or excipients.

* * * * *